(12) United States Patent
Yuers et al.

(10) Patent No.: US 9,038,477 B2
(45) Date of Patent: May 26, 2015

(54) METHOD, APPARATUS AND SYSTEM FOR TESTING THE SELF-SEALING CAPABILITIES OF A CONCRETE SAMPLE

(75) Inventors: Kevin Yuers, Delta (CA); Rishi Gupta, Burnaby (CA); Alireza Biparva, North Vancouver (CA)

(73) Assignee: KHI CAPITAL INC., Vancouver (CA)

( * ) Notice: Subject to any disclaimer, the term of this patent is extended or adjusted under 35 U.S.C. 154(b) by 55 days.

(21) Appl. No.: 13/470,220

(22) Filed: May 11, 2012

(65) Prior Publication Data
US 2013/0008258 A1    Jan. 10, 2013

(30) Foreign Application Priority Data

May 12, 2011   (CA) ..................................... 2740072

(51) Int. Cl.
  *G01N 3/30*    (2006.01)
  *G01N 33/38*   (2006.01)
(52) U.S. Cl.
  CPC ..................................... *G01N 33/38* (2013.01)
(58) Field of Classification Search
  USPC ........................................................ 73/803
  See application file for complete search history.

(56) References Cited

U.S. PATENT DOCUMENTS 4,885,941 A * 12/1989 Vardoulakis et al. ........... 73/794
7,530,396 B1 * 5/2009 Reddy et al. ................. 166/293

OTHER PUBLICATIONS

Authors: C.-M. Aldea, S. P. Shah and A. Karr, Title: Permeability of cracked concrete, Date: Jun. 1999, Publisher: Materials and Structures/Materiauxet Constructions, vol. 32, pp. 370-376.*
Authors: Ravindra Gettu, Barzin Mobasheri, Sergio Carmona, and Daniel C. Jansen, Title: Testing of Concrete Under Closed-Loop Control, Date: 1996, Publisher: Advanced Cement Based Materials, vol. 3, pp. 54-71.*
Authors: Meghdad Hoseini, Vivek Bindiganavile and Nemkumar Banthia, Title: The effect of mechanical stress on permeability of concrete: A review, Date: Feb. 12, 2009, Publisher: Cement & Concrete Composites, vol. 31, pp. 213-220.*
Authors: Victor C. Lia, Yun Mook Lim and Yin-Wen Chan, Title: Feasibility study of a passive smart self-healing cementitious composite, Date: 1998, Publisher: Elsevier Science Ltd., vol. Composites Part B 29B, pp. 819-827.*
Authors: Unknown, Title: Water Permeability of Hardened Concrete, Date: 1998, Publisher: Main Roads Western Australia, pp. 1-7.*
Authors: Kejin Wang, Daniel C. Jansen and Surendra P. Shah, Title: Permeability Study of Cracked Concrete, Date: 1997, Publisher: Cement and Concrete Research. vol. 27, No. 3, pp. 381-393.*

* cited by examiner

*Primary Examiner* — Harshad R Patel
(74) *Attorney, Agent, or Firm* — Nexus Law Group LLP

(57) ABSTRACT

A method, apparatus and system for testing the self-sealing properties of a concrete sample. The method may include providing an apparatus for creating a consistent and reproducible crack in a concrete sample and creating a consistent and reproducible crack in the concrete sample with the apparatus. The method may further include providing a fluidic delivery system that provides a consistent flow of fluid for testing the self-sealing properties of the concrete sample and testing the self-sealing properties of the concrete sample with the system.

17 Claims, 5 Drawing Sheets

METHOD, APPARATUS AND SYSTEM FOR TESTING THE SELF-SEALING CAPABILITIES OF A CONCRETE SAMPLE

FIELD OF THE INVENTION

The invention relates to the field of testing methodology and in particular in relation to a method for testing the self-sealing capabilities of a concrete sample and an apparatus and system used in the method.

BACKGROUND OF THE INVENTION

Concrete is a common building material that is prized for its versatility, strength and durability. However, strength and durability are both compromised in concrete due to damage as a result of water intrusion through cracks, which in turn leads to various destructive processes within concrete—especially concrete containing steel reinforcement. Since concrete is a mixture of various components, including water, and is weak under tension, it is common for concrete to develop cracks due to tension forces caused by shrinking and/or loading. Such resulting cracks provide paths for the easy intrusion of water and waterborne chemicals, which commonly lead to damaging chemical and physical processes and premature deterioration of the concrete.

It has been observed that some cracks in concrete may initially allow the passage of water, but then over time, the flow of water may be reduced and eventually stopped completely. A crack, that formerly allowed the passage of water and subsequently sealed so as to no longer allow the passage of water, is said to have "self-sealed".

Chemical agents are commercially available which claim to enhance the ability of concrete to self-seal. These agents further claim that they allow concrete to self-seal more quickly and also allow self-sealing of cracks that are much wider than those cracks that may self-seal in concrete that do not contain these agents.

Accordingly, a need exists for a method for testing the self-sealing properties of a concrete sample in order to prove or disprove the claims made about these agents. In addition, a reliable test method would allow for the comparison of concrete mixtures, which vary in their ingredients, proportions and other factors contributing to their hardened properties, in so far as these relate to the self-sealing ability of the concrete.

A suitable method for testing the self-sealing properties of a concrete sample has not previously existed. Prior art relating to this subject has failed to achieve acceptable results due to two major missing elements:

1. The ability to produce a concrete sample with consistent, predictable and repeatable crack size and shape. The ability to produce a crack with the same size and shape in each concrete sample is critical to the comparability and validity of test results measured and compared between samples; and
2. The ability to produce a suitable flow of water through a crack in a concrete sample that is consistent between comparable samples, can be accurately measured over time and maintains a constant vertical head pressure over time, independent of flow.

It is an object of the present invention to address these two missing elements. Other objects of the invention will be apparent from the description that follows.

SUMMARY OF THE INVENTION

According to the present invention there is provided a method, apparatus and system for testing the self-sealing properties of a concrete sample. The method may include providing an apparatus for creating a consistent and reproducible crack in the concrete sample and then creating a consistent and reproducible crack in the concrete sample with the apparatus. The method may also include providing a fluidic delivery system that provides a consistent flow of fluid for testing the self-sealing properties of the concrete sample and then testing the self-sealing properties of the concrete sample with the system.

The apparatus for creating a consistent and reproducible crack in a concrete sample may include a base member and first and second opposed support structures connectable to the base. A top member moveable relative to the support structures and being opposed to the base member may be included as part of the apparatus. First and second opposed stabilizer members, each of which are connectable to the first and second opposed support structures, may also be included. Finally, the apparatus may include a first force member connectable to the base and a second force member connectable to the top member.

The method of creating a consistent and reproducible crack in a concrete sample may include placing the concrete sample in the apparatus and aligning the concrete sample in the apparatus so that the first and second force members are centered along a middle-line of the concrete sample. The first and second stabilizer members may then be connected to the first and second opposed support structures to snugly engage the concrete sample. The apparatus may then be placed into a hydraulic press so that said press engages the top member and the press is then operated until a crack is created in the concrete sample.

The fluidic delivery system for testing the self-sealing properties of the concrete sample may include a tank filled with a constant head of fluid and a fluidic distribution device connected to the tank. A fluidic transport device connectable to the distribution device and to the concrete sample may also be included as well as a platform for holding the concrete sample, and fluidic collection means disposed underneath the platform.

The method of testing the self-sealing properties of a concrete sample may include applying a continuous bead of waterproof substance down the outside cracks of the sides of the concrete sample. A waterproof jacket may be secured around the sides of the concrete sample and the sample may be stood upright. A fluidic coupling may be secured to the waterproof jacket adjacent a top portion of the concrete sample and the fluidic coupling may be affixed to the fluidic delivery system. The fluidic delivery system may be operated and a flow rate may be recorded as fluid passes through the concrete sample.

Other aspects of the invention will be appreciated by reference to the detailed description of the preferred embodiment and to the claims that follow.

BRIEF DESCRIPTION OF THE DRAWINGS

The preferred embodiment of the invention will be described by reference to the drawings thereof in which.

DESCRIPTION OF THE PREFERRED EMBODIMENT OF THE INVENTION

The invention relates to a method for testing the self-sealing properties of a concrete sample. To initiate the test, an apparatus for creating a consistent and reproducible crack in the concrete sample is provided.

Figure 1:
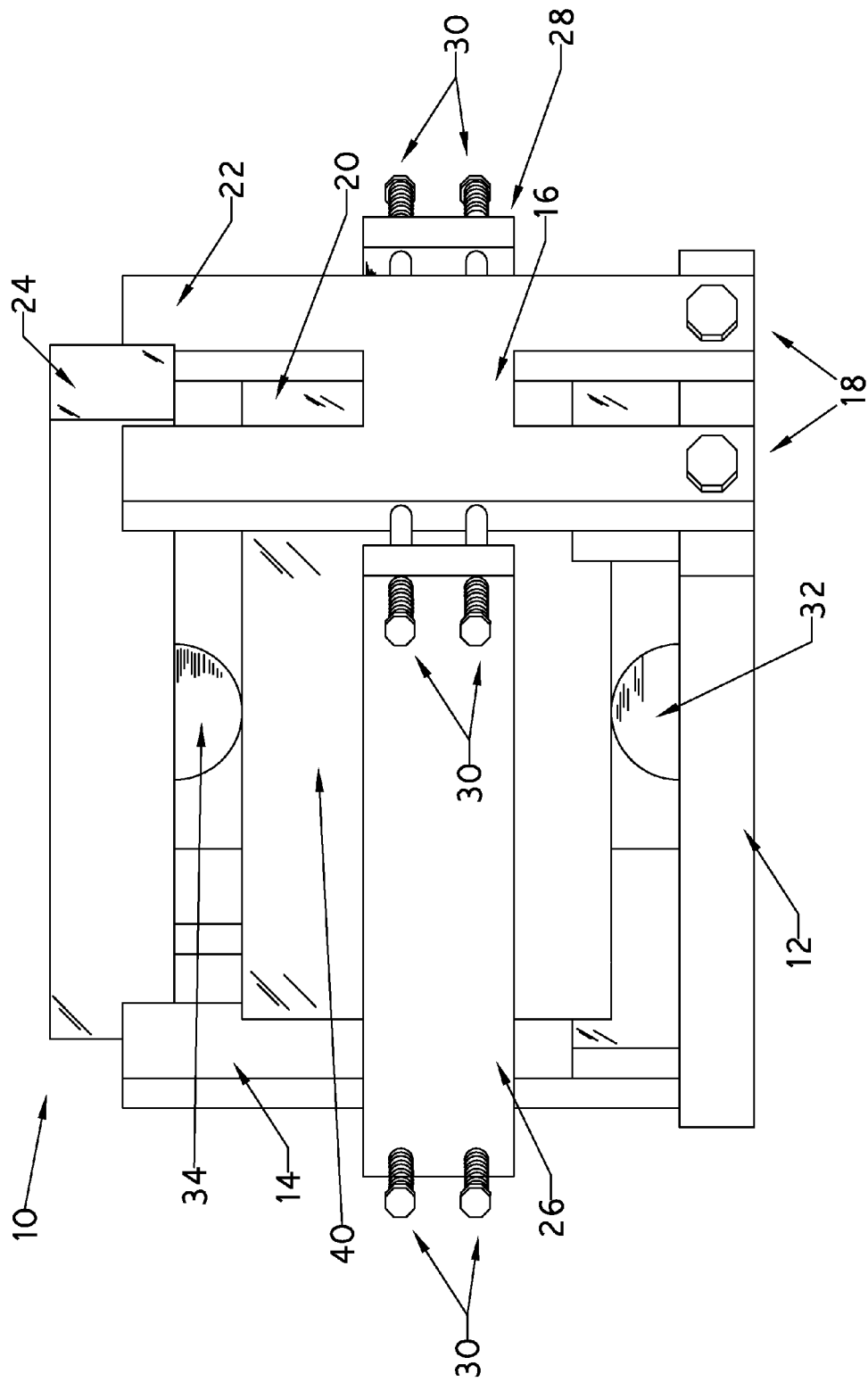
FIG. 1 is perspective view of an embodiment of an apparatus for creating a consistent and reproducible crack in a concrete sample.
Figure 2:
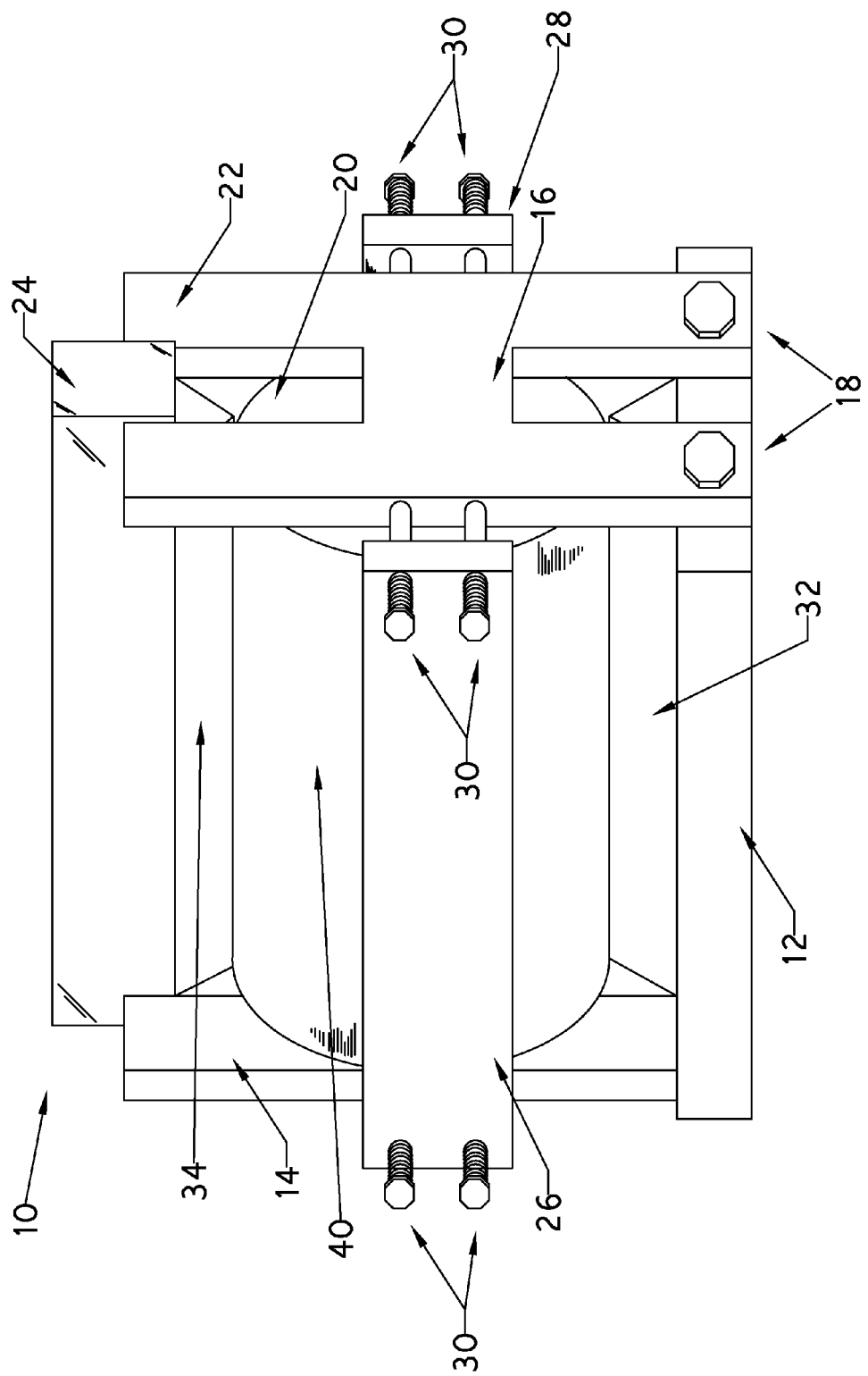
FIG. 2. is a perspective view of another embodiment of an apparatus for creating a consistent and reproducible crack in a concrete sample.

Referring to FIGS. 1 and 2, the apparatus includes a jig frame 10 which includes a base 12 and first 14 and second 16 opposed support structures emanating from the base. First 14 and second 16 opposed support structures may be integrally formed with the base 12 or may be connectable to the base via fasteners 18, as depicted. Preferably as depicted, each of the first 14 and second 16 opposed support structures include a notched section 20 adjacent the respective top portion 22 of the support structures. A top member 24 is disposed and is moveable within the frame 10. Preferably, top member 24 is dimensioned to fit within the notched sections 22 of the first 14 and second 16 opposed support structures. First 26 and second 28 opposed stabilizer members are each connectable to the first 14 and second 16 support structures via fasteners 30, as depicted.

The apparatus also includes a first force member 32 connectable to the base 12 and a second force member 34 connectable to the top member 24. As depicted in FIG. 1, the first 32 and second 34 force members are merely ball bearings whereas depicted in FIG. 2, the first and second force members are cutting blades. FIG. 1 shows the jig 10 in its direct compression cracking configuration with a concrete sample 40 placed upright. The direct compression configuration uses ball bearings to create high pressure point loads on the upper and lower faces of a concrete sample 40. The crack patterns here, could be radial or linear, passing though the center of the sample 40. FIG. 2 shows the jig 10 in its indirect tension configuration with the concrete sample 40 placed on its side. The indirect tension configuration uses the cutting edges to create a line of high stress concentration on each side of the sample 40. This causes a single linear crack from one face of the sample 40 to the other.

Figure 3:
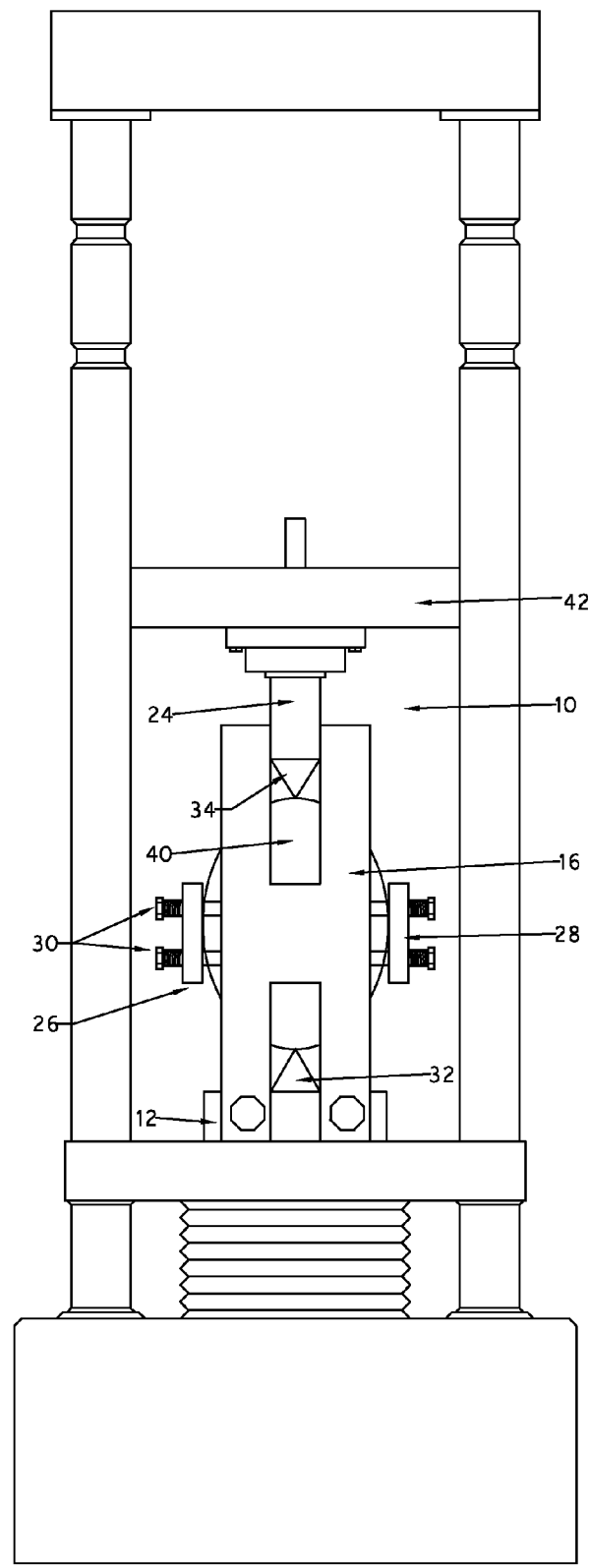
FIG. 3 is a plan view of the apparatus of FIG. 2 engaged in a press.

Once the apparatus is constructed, a consistent and reproducible crack may be created in the concrete sample 40. Referring to FIG. 3, after the sample 40 and first 32 and second 34 force members have been wiped clean of any excess concrete debris or dust, the sample is placed within the jig 10 either upright, as depicted in FIG. 1, or on its side as depicted in FIG. 2. Care is taken to align the concrete sample 40 in the jig 10 so that the first 32 and second force 34 members are centered along a middle-line of the concrete sample 40. Care is also taken to ensure that the first 32 and second 34 force members are not aligned over any large void or aggregate pieces in the sample 40. The first 26 and second 28 opposed stabilizer members may further be connected to the first 14 and second 16 opposed support structures to snugly engage the concrete sample 40. To aid in the engagement of the first 26 and second 28 opposed stabilizer members to the sample 40, each of the stabilizer members may include a resilient material (not depicted), such as foam, attached to the engaging sides of the stabilizer members. Alternatively, the fasteners 30 may be a biasing device such as by including a spring as shown in FIGS. 1 to 3. Once the sample 40 is snugly placed into the jig 10 and properly aligned, the jig may then be placed into a hydraulic press 42 so that the press engages the top member 24. Once engaged, the press 42 is then operated to plunge the top member 24 and second 34 force member into the sample 40 until a crack is created. To disperse the force created by the press 42 more evenly across the top member 24 and hence the sample 40, a steel plate (not depicted) may be inserted between the press and top member. Preferably, a loading rate of 20 kN/min should be applied with the press 42 onto the sample 40.

Once a consistent and reproducible crack in the sample 40 has been created with the jig 10, a fluidic delivery system for testing the self-sealing properties of the sample is provided.

Figure 4:
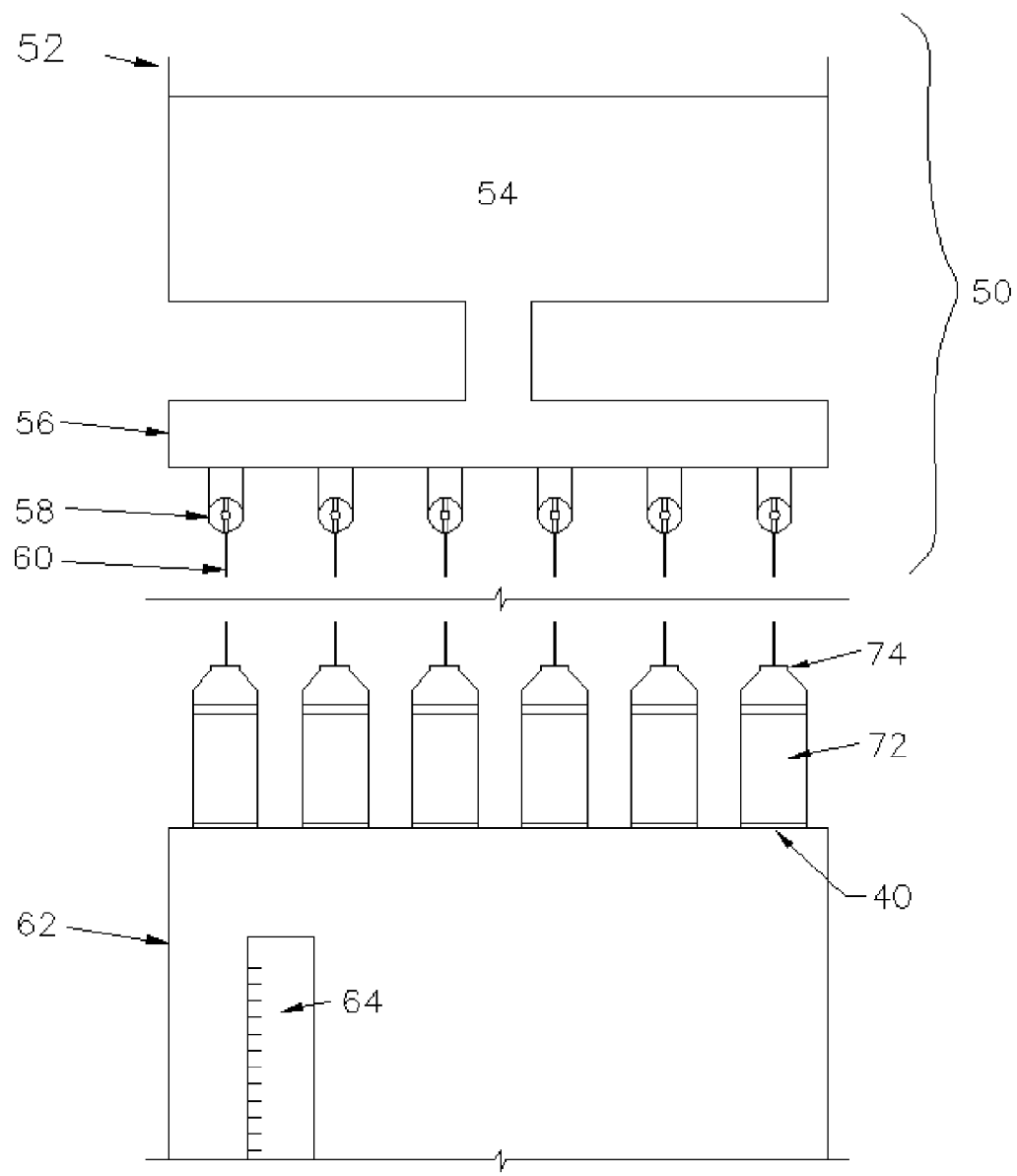
FIG. 4 is a schematic diagram of a fluidic delivery system for testing the self-sealing properties of a concrete sample.

Referring to FIG. 4, a fluidic delivery system 50 that provides a consistent flow of fluid for testing the self-sealing properties of the sample 40 includes a tank 52 filled with a constant head of fluid 54. A fluidic distribution device 56 is connected to the tank 50. The distribution device 56 is conventionally constructed and includes a reservoir and distribution manifold (not depicted)—each of which must be elevated above the concrete sample so as to produce a consistent hydraulic head. The reservoir must be kept filled to a constant height by using a common float valve connected to a water supply, similar to what you find in a toilet reservoir. The distribution device 56 also includes a valve 58 to control the volumetric flow of the fluid 54 to the sample 40. A fluidic transport device 60, such a hose or other conduit device, is connectable to the valve 58 and to the sample 40. To hold the sample 40 in place during testing, the system 50 also includes a platform 62 which is adapted to allow the fluid 54 to pass through; for example, platform 62 may simply be a wire rack. Finally, the system 50 includes fluidic collection means 64 disposed underneath the platform 62. Preferably, the fluidic collection means 64 is a device that enables the user to measure the volume of fluid that passes through the sample 40, such as a graduated cylinder or other measured container.

Once the fluidic delivery system 50 has been provided, testing the self-sealing properties of the sample 40 may commence. A continuous bead of waterproof substance, such as silicone, is applied down the outside cracks of the longitudinal sides of the concrete sample 40. The waterproof substance is preferably void free and the sample 40 should sit for some time after application of the waterproof substance to enable the substance to cure. Once the substance has cured, the sample 40 is secured with a waterproof jacket 72 around its sides. The sample 40 is then stood upright and secured to a fluidic coupling 74 adjacent a top portion of the sample 40. The fluidic coupling 74 may then be affixed to the fluidic transport device 60 and operation of the system 50 may commence. Finally, the flow rate of fluid as it passes through the sample 40 may then be recorded.

Figure 5:
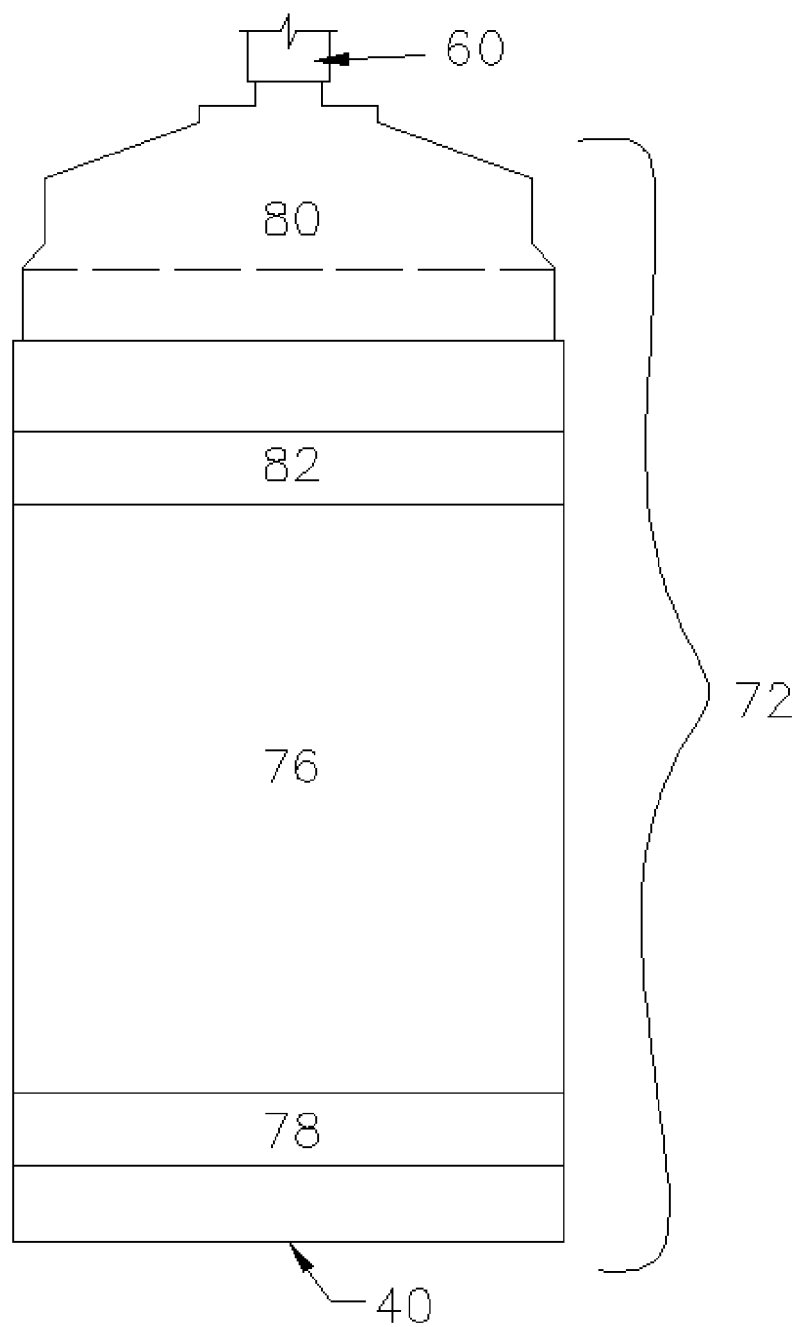
FIG. 5 is a plan view of a jacket attached to a concrete sample and a fluidic transport device of FIG. 4.

Referring to FIG. 5, jacket 72 includes a waterproof sleeve 76 (preferably made of rubber) secured around the sample 40 with a lower clamp 78. Jacket 72 also includes a fluidic coupling 80 (preferably constructed from PVC) which covers the top portion of the sample 40 and is adapted to engage with the fluidic transport device 60 using conventional means. To install coupling 80 onto the sample 40, it is first slid over the top portion of the sample 40 and underneath the top of portion of sleeve 76. Both the top portion of the sleeve 76 and coupling 80 may then be secured to the sample 40 with an upper clamp 82.

To achieve the goal of creating a method for testing the self-sealing properties of the concrete sample 40 it is important that the crack has a constant width throughout the sample 40 and be small enough to allow for self-sealing to occur. Generally, concrete is weakest in tension; therefore a smaller load is required to crack the sample 40. Given the consistency of application and low load requirements, preferably a jig 10 configuration as depicted in FIG. 2 is used for testing the self sealing properties of the sample 40.

The following table gives the mix proportions used to prepare the samples 40.

| Mix Proportions [kg/m³] | |
| --- | --- |
| Portland Cement | 340 |
| Gravel (~10 mm) | 1120 |
| Sand | 820 |
| Water | 190 |

For comparison testing, some samples include a substance known commercially as KIM®. In these instances, the samples 40 were made using the same mix design, except 2% of the cement was substituted with an equivalent weight of KIM®. KIM® is a cement-based admixture that is added to fresh concrete before placement. KIM® has been in commercial use for over 35 years as waterproofing protection in concrete structures. The addition of KIM® in a concrete mix eliminates the need for external waterproofing membranes. When exposed to water, KIM® reacts with unhydrated cement to form a crystalline structure that fills the voids and pores in hardened concrete. The crystals form a tight matrix that turns the concrete into an impermeable barrier that prevents water intrusion. When concrete cracks due to shrinkage, settlement, etc., KIM® reactivates and crystal growth resumes until the crack seals. This unique property gives KIM® concrete the ability to "self-seal".

Following completion of the sample 40 mix, a sample may be molded into shape. Preferably the sample 40 is in the shape of a cylinder having a 4" diameter with a length of 6". As those skilled in the art will appreciate, any suitable sample shape will suffice. As those skilled in the art will also appreciate, the sample 40 may also includes regions to allow for the first 32 and second force members 32 to engage the sample. For example, when the first 32 and second force members 34 are cutting blades, the regions may be longitudinal notches made into the sample 40. To construct a notched sample, a mold may consist of angles that are attached to the sides of a standard 4"×6" mold. Preferably, samples older than 2 days and less than 7 days are used in the self-sealing test.

Flow measurements may be taken in real time using flow meters and manual measurements. The flow meters may have a flow range of 100-2000 ml/min. Samples 40 with smaller cracks, less than 0.4 mm, may have smaller flows that require manual measurement. Optionally, instead of measuring the volume of the fluid in the fluidic collection means 64, it may be advantageous to physically measure the flow using a graduated cylinder and a stopwatch. Using this measurement approach may eliminate the lost volume due to evaporation and can provide an exact flow at one instance instead of an average across hours of flow.

It is recommended that a FLR-1618A-V2 Omega Engineering™ flow meter or suitable substitute be used to measure the flow. This type of meter measures flows from 4-200 ml/min. Alternatively, a FTB601-B Omega Engineering™ flow meter or suitable substitute may be used to measure the flow. This type of meter measures flows from 100-2000 ml/min.

To process the flow meter output frequencies, it is possible to use a National Instruments™ USB-6210 multifunction data acquisition board (DAQ). A flow meter produces a unique frequency corresponding to the actual flow. The DAQ can take as input the raw digital frequency, count the incoming pulses, and output a scaled number via a task to DASYlab 10.

It will thus be seen that a new and novel method, apparatus and system for testing the self-sealing properties of a concrete sample has been illustrated and described and it will be apparent to those skilled in the art that various changes and modifications may be made therein without departing from the spirit of the invention.

What is claimed is:

1. A method for testing self-sealing properties of a concrete sample, the method comprising:
   providing an apparatus for creating a consistent and reproducible crack in the concrete sample, said apparatus comprising a base, first and second opposed support structures projecting from said base, a top member moveable relative to said support structures and being opposed to said base, and first and second opposed stabilizers, each said stabilizer being connectable to said support structures by a biasing device operable to fasten said each stabilizer to said support structures, said biasing device comprising a spring such that said stabilizers resiliently engage the concrete sample;
   creating a consistent and reproducible crack in the concrete sample with said apparatus;
   providing a fluidic delivery system that provides a flow of fluid for testing the self-sealing properties of the concrete sample; and
   testing the self-sealing properties of the concrete sample with said fluidic delivery system.

2. The method of claim 1 wherein creating a consistent and reproducible crack in the concrete sample with said apparatus comprises:
   placing the concrete sample in said apparatus such that the concrete sample is centrally aligned relative to first and second force members of said apparatus, said first force member being connected to said base and said second force member being connected to said top member;
   connecting said first and second stabilizers to said first and second support structures to resiliently engage the concrete sample;
   placing said apparatus into a hydraulic press so that said press engages said top member; and
   operating said press until the crack is created in the concrete sample.

3. The method of claim 2 wherein operating said press until the crack is created in the concrete sample comprises contacting the concrete sample with respective cutting blades of said first and second force members.

4. The method of claim 1 wherein providing a fluidic delivery system that provides a flow of fluid for testing the self-sealing properties of the concrete sample comprises providing said fluidic delivery system comprising:
   a tank for containing a constant head of said fluid;
   a fluidic distribution device for controlling said flow of fluid, said fluidic distribution device being connected to said tank;
   a conduit for transporting said fluid to the concrete sample, said conduit being connectable to said fluidic distribution device and to the concrete sample;
   a platform for holding the concrete sample; and
   a fluidic collection device for collecting said fluid after said fluid flows through the concrete sample, said fluidic collection device being disposed underneath said platform.

5. The method of claim 4 wherein providing said fluidic delivery system comprises providing said fluidic delivery system when said fluidic distribution device comprises a valve for controlling the volume of said flow of fluid from said fluidic distribution device.

6. The method of claim 4 wherein providing said fluidic delivery system comprises providing said fluidic delivery system when said conduit is removably connectable to a fluidic coupling dimensioned for being secured to the concrete sample.

7. The method of claim 4 wherein providing said fluidic delivery system comprises providing said fluidic delivery system when said fluidic collection device is operable to indicate the volume of said fluid having passed through the concrete sample.

8. The method of claim 1 wherein testing the self-sealing properties of the concrete sample with said fluidic delivery system comprises:
   applying a continuous bead of waterproof substance to the outside of the concrete sample along the crack;
   securing a waterproof jacket around the outside of the concrete sample;
   standing the concrete sample vertically upright;
   securing a fluidic coupling to said waterproof jacket adjacent the top portion of the concrete sample;
   affixing said fluidic coupling to said fluidic delivery system;
   operating said fluidic delivery system to produce a flow of fluid; and
   recording a flow rate of said fluid after said fluid passes through the concrete sample.

9. The method of claim 8 wherein operating said fluidic delivery system to produce a flow of fluid comprises passing said fluid from said fluidic delivery system to said fluidic coupling.

10. The method of claim 8 further comprising holding the concrete sample by a platform such that said fluid passing through the concrete sample passes into a fluidic collection device.

11. The method of claim 1 further comprising connecting said first and second stabilizers to said first and second support structures to resiliently engage the concrete sample.

12. An apparatus for creating a crack in a concrete sample to facilitate testing self-sealing properties of the concrete sample, the apparatus comprising:
   a base;
   first and second opposed support structures projecting from said base;
   a top member moveable relative to said support structures and being opposed to said base;
   first and second opposed stabilizers, each of which are connectable to said first and second opposed support structures by a biasing device operable to fasten each said stabilizer to said support structures, said biasing device comprising a spring such that said stabilizers resiliently engage the concrete sample; and
   a first force member connected to said base and a second force member connected to said top member.

13. The apparatus of claim 12 wherein said first and second support structures are removably connectable to said base.

14. The apparatus of claim 12 wherein said first and second support structures comprise respective notches for receiving said top member, said top member being moveable within said notches.

15. The apparatus of claim 12 wherein each of said first and second force members comprises a cutting blade.

16. An apparatus for creating a crack in a concrete sample to facilitate testing the self-sealing properties of the concrete sample, the apparatus comprising:
   a base;
   first and second opposed support structures projecting from said base;
   a top member moveable relative to said support structures and being opposed to said base;
   first and second opposed stabilizers, each of which are connectable to said first and second opposed support structures; and
   a first force member connected to said base and a second force member connected to said top member,
wherein each of said first and second force members comprises a ball bearing.

17. A method of creating a crack in a concrete sample to facilitate testing the self-sealing properties of the concrete sample, the method comprising:
   placing the concrete sample in a jig such that the concrete sample is centrally aligned relative to first and second force members of said jig, said jig comprising a base, first and second opposed support structures projecting from said base, a top member moveable relative to said support structures and being opposed to said base, first and second opposed stabilizers each of which are connectable to said first and second opposed support structures, said first force member connected to said base and said second force member connected to said top member;
   connecting said first and second stabilizers to said first and second support structures to engage the concrete sample;
   placing said jig into a hydraulic press so that said press engages said top member; and
   operating said press until the crack is created in the concrete sample,
wherein operating said press until the crack is created in the concrete sample comprises contacting the concrete sample with respective ball bearings of said first and second force members.

* * * * *